US008531100B2

(12) United States Patent
Herron et al.

(10) Patent No.: US 8,531,100 B2
(45) Date of Patent: Sep. 10, 2013

(54) DEUTERATED COMPOUNDS FOR LUMINESCENT APPLICATIONS

(75) Inventors: Norman Herron, Newark, DE (US); Vsevolod Rostovtsev, Swarthmore, PA (US); Jeffrey A. Merlo, Wilmington, DE (US); Michael Henry Howard, Jr., Montchanin, DE (US); Adam Fennimore, Wilmington, DE (US); Weiying Gao, Landenberg, PA (US); Kalindi Dogra, Wilmington, DE (US); Nora Sabina Radu, Landenberg, PA (US); Weishi Wu, Landenberg, PA (US); Eric Maurice Smith, Hockessin, DE (US); Daniel David Lecloux, Wilmington, DE (US)

(73) Assignee: E I du Pont de Nemours and Company, Wilmington, DE (US)

( * ) Notice: Subject to any disclaimer, the term of this patent is extended or adjusted under 35 U.S.C. 154(b) by 497 days.

(21) Appl. No.: 12/643,511

(22) Filed: Dec. 21, 2009

(65) Prior Publication Data

US 2010/0187983 A1   Jul. 29, 2010

Related U.S. Application Data

(60) Provisional application No. 61/139,834, filed on Dec. 22, 2008, provisional application No. 61/176,141, filed on May 7, 2009.

(51) Int. Cl.
*H01J 1/63* (2006.01)
*C07C 211/61* (2006.01)

(52) U.S. Cl.
USPC .................. 313/504; 564/426; 564/427

(58) Field of Classification Search
USPC .......................................... 313/504
See application file for complete search history.

(56) References Cited

U.S. PATENT DOCUMENTS

| 4,053,311 | A  | 10/1977 | Limburg |
| 5,247,190 | A  | 9/1993 | Friend et al. |
| 5,378,519 | A  | 1/1995 | Kikuchi et al. |
| 5,408,109 | A  | 4/1995 | Heeger et al. |
| 6,303,238 | B1 | 10/2001 | Thompson et al. |
| 6,670,645 | B2 | 12/2003 | Grushin et al. |
| 6,852,429 | B1 | 2/2005 | Li et al. |
| 6,875,524 | B2 | 4/2005 | Hatwar et al. |
| 7,075,102 | B2 | 7/2006 | Grushin et al. |
| 7,173,131 | B2 | 2/2007 | Saitoh et al. |
| 7,351,358 | B2 | 4/2008 | Hsu et al. |
| 7,358,409 | B2 | 4/2008 | Saitoh et al. |
| 7,365,230 | B2 | 4/2008 | Herron et al. |
| 7,375,250 | B2 | 5/2008 | Saitoh et al. |
| 7,402,681 | B2 | 7/2008 | Ong et al. |
| 7,431,866 | B2 | 10/2008 | Hsu et al. |
| 7,462,298 | B2 | 12/2008 | Hsu et al. |
| 7,491,450 | B2 | 2/2009 | Okinaka et al. |
| 7,528,542 | B2 | 5/2009 | Kawamura et al. |
| 7,586,006 | B2 | 9/2009 | Funahashi |
| 7,651,786 | B2 | 1/2010 | Matsuura |
| 7,651,788 | B2 | 1/2010 | Seo et al. |
| 7,709,104 | B2 | 5/2010 | Saitoh et al. |
| 8,026,665 | B2 | 9/2011 | Kim et al. |
| 2002/0076576 | A1 | 6/2002 | Li et al. |
| 2003/0072966 | A1 | 4/2003 | Hosokawa et al. |
| 2003/0118866 | A1 | 6/2003 | Oh et al. |
| 2003/0138657 | A1 | 7/2003 | Li |
| 2004/0102577 | A1 | 5/2004 | Hsu et al. |
| 2004/0106003 | A1 | 6/2004 | Chen et al. |
| 2004/0106004 | A1 | 6/2004 | Li |
| 2004/0121184 | A1 | 6/2004 | Thompson et al. |
| 2004/0127637 | A1 | 7/2004 | Hsu et al. |
| 2004/0209118 | A1 | 10/2004 | Seo et al. |
| 2004/0263067 | A1 | 12/2004 | Saitoh et al. |
| 2005/0031898 | A1 | 2/2005 | Li et al. |
| 2005/0064233 | A1 | 3/2005 | Matsuura et al. |
| 2005/0158577 | A1 | 7/2005 | Ishibashi et al. |
| 2005/0184287 | A1 | 8/2005 | Herron et al. |
| 2005/0205860 | A1 | 9/2005 | Hsu et al. |
| 2005/0244670 | A1 | 11/2005 | Saitoh et al. |
| 2005/0245752 | A1 | 11/2005 | Conley et al. |
| 2006/0033421 | A1 | 2/2006 | Matsuura et al. |
| 2006/0043858 | A1 | 3/2006 | Ikeda et al. |
| 2006/0052641 | A1* | 3/2006 | Funahashi .................. 564/426 |
| 2006/0103298 | A1 | 5/2006 | Lee |
| 2006/0113528 | A1 | 6/2006 | Okinaka et al. |
| 2006/0115678 | A1 | 6/2006 | Saitoh et al. |
| 2006/0121312 | A1 | 6/2006 | Yamada et al. |
| 2006/0127698 | A1 | 6/2006 | Tokailin et al. |
| 2006/0134459 | A1 | 6/2006 | Huo |
| 2006/0152146 | A1 | 7/2006 | Funahashi |

(Continued)

FOREIGN PATENT DOCUMENTS

| CN | 1668719 A | 9/2005 |
| CN | 1711334 A | 12/2005 |

(Continued)

OTHER PUBLICATIONS

CRC Handbook of Chemistry and Physics, 81$^{st}$ Edition (2000-2001) (Book Not Included).
"Flexible light-emitting diodes made from soluble conducting polymer" Nature, vol. 357, pp. 477 479 (Jun. 11, 1992).
Kirk-Othmer Encyclopedia of Chemical Technology, Fourth Edition, vol. 18, pp. 837-860, 1996 Y. Wang.
Markus, John, Electronics and Nucleonics dictionary, 470 and 476 (McGraw-Hill 1966).
Muller, U.; Adam, M.; Mullen, K. Chem. Ber. 1994, 127, 437-444.

(Continued)

*Primary Examiner* — Yong Chu

(57) ABSTRACT

This invention relates to deuterated compounds that are useful in electroluminescent applications. It also relates to electronic devices in which the active layer includes such a deuterated compound.

13 Claims, 1 Drawing Sheet

(56) References Cited

U.S. PATENT DOCUMENTS

| | | |
|---|---|---|
| 2006/0158102 A1 | 7/2006 | Kawamura et al. |
| 2006/0159838 A1 | 7/2006 | Kowalski et al. |
| 2006/0194074 A1 | 8/2006 | Funahashi |
| 2006/0210830 A1 | 9/2006 | Funahashi et al. |
| 2006/0217572 A1 | 9/2006 | Kawamura et al. |
| 2006/0267488 A1 | 11/2006 | Saitoh et al. |
| 2006/0284140 A1 | 12/2006 | Breuning et al. |
| 2007/0031701 A1 | 2/2007 | Nakashima et al. |
| 2007/0063638 A1 | 3/2007 | Tokairin et al. |
| 2007/0114917 A1 | 5/2007 | Funahashi et al. |
| 2007/0155991 A1 | 7/2007 | Funahashi |
| 2007/0200123 A1 | 8/2007 | Yamamichi et al. |
| 2007/0236137 A1 | 10/2007 | Funahashi |
| 2007/0247063 A1 | 10/2007 | Murase et al. |
| 2007/0255076 A1 | 11/2007 | Ito et al. |
| 2007/0292713 A9 | 12/2007 | Dobbs et al. |
| 2007/0298530 A1 | 12/2007 | Feehery |
| 2008/0049413 A1 | 2/2008 | Jinde et al. |
| 2008/0071049 A1 | 3/2008 | Radu et al. |
| 2008/0086012 A1 | 4/2008 | Egawa et al. |
| 2008/0102311 A1 | 5/2008 | Funahashi |
| 2008/0114178 A1 | 5/2008 | Kawakami et al. |
| 2008/0191614 A1 | 8/2008 | Kim et al. |
| 2008/0233433 A1 | 9/2008 | Igarashi et al. |
| 2008/0286605 A1 | 11/2008 | Takeda |
| 2008/0303425 A1 | 12/2008 | Rostovtsev et al. |
| 2008/0303428 A1 | 12/2008 | Rostovtsev et al. |
| 2008/0315754 A1 | 12/2008 | Kawamura et al. |
| 2009/0058270 A1 | 3/2009 | Ito et al. |
| 2009/0058279 A1 | 3/2009 | Takeda |
| 2009/0134781 A1 | 5/2009 | Jang et al. |
| 2009/0295274 A1 | 12/2009 | Hwang et al. |
| 2010/0117028 A1 | 5/2010 | Takeshima et al. |
| 2010/0187505 A1* | 7/2010 | Stoessel et al. ............. 257/40 |
| 2010/0187981 A1 | 7/2010 | Gao et al. |
| 2011/0147718 A1 | 6/2011 | Howard, Jr. et al. |
| 2012/0037898 A1 | 2/2012 | Wu et al. |

FOREIGN PATENT DOCUMENTS

| | | | |
|---|---|---|---|
| CN | 1768029 A | | 5/2006 |
| CN | 1957646 A | | 5/2007 |
| CN | 101679209 A | | 3/2010 |
| EP | 0443861 B1 | | 5/1995 |
| EP | 1061112 A1 | | 12/2000 |
| EP | 765106 A2 | | 11/2002 |
| EP | 1317005 A2 | | 6/2003 |
| EP | 1541657 A1 | | 6/2005 |
| EP | 1561794 A1 | | 8/2005 |
| EP | 1612202 A1 | | 1/2006 |
| EP | 1792893 A1 | | 6/2007 |
| EP | 1860096 A1 | | 11/2007 |
| EP | 1932895 A1 | | 6/2008 |
| EP | 2093271 A1 | | 8/2009 |
| EP | 2067766 A1 | | 10/2009 |
| EP | 2067767 A1 | | 10/2009 |
| JP | 07249490 A | | 9/1995 |
| JP | 08020770 A | | 1/1996 |
| JP | 08053397 A | | 2/1996 |
| JP | 2001131541 A | | 5/2001 |
| JP | 2002012861 A | | 1/2002 |
| JP | 2004-10550 A | | 1/2004 |
| JP | 2006016384 A | | 1/2006 |
| JP | 2006052323 A | | 2/2006 |
| JP | 2006-151844 A | | 6/2006 |
| JP | 2006-219392 A | | 8/2006 |
| JP | 2006256979 A | | 9/2006 |
| JP | 2007-186449 A | | 7/2007 |
| JP | 2009161469 A | | 7/2009 |
| JP | 2009161470 A | | 7/2009 |
| KR | 10-2009-0046731 A | | 5/2009 |
| KR | 10-2009-0086015 A | | 8/2009 |
| KR | 10-2009-0086920 A | | 8/2009 |
| KR | 10-2009-0093897 A | | 9/2009 |
| WO | 0070655 A2 | | 11/2000 |
| WO | 0141512 A1 | | 6/2001 |
| WO | 03008424 A1 | | 1/2003 |
| WO | 03040257 A1 | | 5/2003 |
| WO | 03063555 A1 | | 7/2003 |
| WO | 03091688 A2 | | 11/2003 |
| WO | 2004016710 A1 | | 2/2004 |
| WO | 2004018587 A1 | | 3/2004 |
| WO | 2004018588 A1 | | 3/2004 |
| WO | 2004044088 A1 | | 5/2004 |
| WO | 2005000787 A1 | | 1/2005 |
| WO | 2005049546 A1 | | 6/2005 |
| WO | WO2005/052027 A1 | | 6/2005 |
| WO | 2005086539 A1 | | 9/2005 |
| WO | 2005117500 A1 | | 12/2005 |
| WO | 2006025273 A1 | | 3/2006 |
| WO | 2006082705 A1 | | 8/2006 |
| WO | 2006098080 A1 | | 9/2006 |
| WO | 2006112582 A1 | | 10/2006 |
| WO | 2006121237 A1 | | 11/2006 |
| WO | 2007021117 A1 | | 2/2007 |
| WO | 2007032162 A1 | | 3/2007 |
| WO | WO2007-100096 A1 | | 9/2007 |
| WO | WO2007-105917 A1 | | 9/2007 |
| WO | WO2007/108666 A1 | | 9/2007 |
| WO | WO 2007108666 A1 * | | 9/2007 |
| WO | 2008023623 A1 | | 2/2008 |
| WO | 2008105472 A1 | | 9/2008 |
| WO | 2008147721 A1 | | 12/2008 |
| WO | WO2008-149968 A1 | | 12/2008 |
| WO | 2009018009 A1 | | 2/2009 |
| WO | WO2009/028902 A2 | | 3/2009 |
| WO | WO2009-055628 A1 | | 4/2009 |
| WO | 2009067419 A1 | | 5/2009 |
| WO | 2010059837 A2 | | 5/2010 |
| WO | 2010068865 A2 | | 6/2010 |
| WO | 2010071362 A2 | | 6/2010 |
| WO | 2010099534 A2 | | 9/2010 |
| WO | 2010135403 A2 | | 11/2010 |

OTHER PUBLICATIONS

International Search Report, Korean Intellectual Property Office, Daejeon, Republic of Korea, in PCT/2009/068928, PCT Counterpart of the Present U.S. Appl. No. 12/643,511, Hyun Shik Oh, Authorized Officer, Aug. 17, 2010.

International Search Report, Korean Intellectual Property Office, Daejeon, Republic of Korea, in PCT/2009/068918, PCT copending U.S. Appl. No. 12/643,403, Jun Gyu Kim, Authorized Officer, Jul. 26, 2010.

International Search Report, Korean Intellectual Property Office, Daejeon, Republic of Korea, in PCT/2010/025764, PCT copending U.S. Appl. No. 12/714,880, Hyun Shik Oh, Authorized Officer, Sep. 27, 2010.

International Search Report, Korean Intellectual Property Office, Daejeon, Republie of Korea, PCT/US2009/068921, PCT copending U.S. Appl. No. 12/643,486, Hyun Shik Oh, Authorized Officer, Aug. 5, 2010.

International Search Report, Korean Intellectual Property Office, Daejeon, Republic of Korea, in PCT/2009/068922, PCT copending U.S. Appl. No. 12/643,567, Hyun Shik Oh, Authorized Officer, Oct. 20, 2010.

International Search Report, Korean Intellectual Property Office, Daejeon, Republic of Korea, in PCT/2010/035356, PCT copending U.S. Appl. No. 12/782,781, Hyun Shik Oh, Authorized Officer, Dec. 24, 2010.

International Search Report, Korean Intellectual Property Office, Daejeon, Republic of Korea, in PCT/2009/068945, PCT copending U.S. Appl. No. 12/643,420, Hyun Shik Oh, Authorized Officer, Sep. 27, 2010.

International Search Report, Korean Intellectual Property Office, Daejeon, Republic of Korea, in PCT/2009/068950, PCT copending U.S. Appl. No. 12/643,449, Hyun Shik Oh, Authorized Officer, Jan. 3, 2011.

International Search Report, Korean Intellectual Property Office, Daejeon, Republic of Korea, in PCT/2009/068956, PCT copending U.S. Appl. No. 12/643,487, Hyun Shik Oh, Authorized Officer, Sep. 6, 2010.

International Search Report, Korean Intellectual Property Office, Daejeon, Republic of Korea, in PCT/2009/069255, PCT copending U.S. Appl. No. 12/643,459, Hyun Shik Oh, Authorized Officer, Aug. 13, 2010.

International Search Report, Korean Intellectual Property Office, Daejeon, Republic of Korea, in PCT/2009/068976, PCT copending U.S. Appl. No. 12/643,515, Bum Soo Kim, Authorized Officer, Jan. 28, 2011.

Beckmann et al., "Methyl Reorientation in Solid 3-ethychrysene and 3-isopropylesene; Solid State Nuclear Magnetic Resonance," 1998; vol. 12; pp. 251-256.

Carey et al., Structure and Mechanisms; Advanced Organic Chemistry, Part A, 5th Edition, pp. 142-145, (2007).

Danel et al., "Blue-Emitting Anthracenes with End-Capping Diarylamines," Chem. Mater., 2002, vol. 14, pp. 3860-3865.

Kim et al., "Synthesis and Electroluminescent Properties of Highly Efficient Anthracene Derivatives with Bulky Side Groups," Organic Electronics, 2009, vol. 10, No. 5, pp. 822-833.

Klaerner et al., "Cross-Linkable Polymers Based on Dialkylfluorenes," Chemistry of Materials, 1999, 11, pp. 1800-1805.

Kodomari et al., "Selective Halogenation o f Aromatic Hydrocarbons," Journal of Organic Chemistry,1988, vol. 53, p. 2093.

Negishi et al; III.2.15 Palladium Catalyzed Conjugate Substitution; Handbook of Organopalladium Chemistry for Organic Synthesis, 2000, vol. 1, pp. 767-789.

Tong et al., "Enhancement of OLED Efficiencies and High-Voltage Stabilities of Light-Emitting Materials by Deuteration," Journal of Physical Chemistry, 2007, vol. 111, pp. 3490-3494.

Weine et al., "Reactions of an O-Quinone Monoimide with Anthracenes, Phencyclone, and 1,3-Diphenylisobenzofuran," Journal of Organic Chemistry, 1989, vol. 54, pp. 5926-5930.

Extended European Search Report for Application No. EP 09833870.0; Feb. 21, 2012.

International Search Report for Application No. PCT/US2011/064654, published as WO2012/082743; Jan Ziegler, Authorized Officer, EPO; May 31, 2012.

International Search Report, Korean Intellectual Property Office, Daejeon, Republic of Korea, Hyun Shik Oh, Authorized Offier, Dec. 24, 2010, in PCT/US10/035364, PCT counterpart of co-pending U.S. Appl. No. 13/265,025.

International Search Report, European Patent Office, Rijswijk NL, in PCT/2008/063811, PCT copending U.S. Appl. No. 12/121,883, Csaba A. Nemes, Authorized Officer, Jul. 29, 2008.

International Search Report, European Patent Office, Rijswijk NL, in PCT/2008/065091, PCT copending U.S. Appl. No. 12/129,760, Alina Sen, Authorized Officer, Oct. 23, 2008.

International Search Report, European Patent Office, Rijswijk NL, in PCT/2008/065187, PCT copending U.S. Appl. No. 12/129,753, Cecile Vanier, Authorized Officer, Feb. 10, 2008.

International Search Report, Korean Intellectual Property Office, Daejeon, Republic of Korea, in PCT/2009/065163, PCT copending U.S. Appl. No. 13/120,001, Hyun Shik Oh, Authorized Officer, May 19, 2010.

International Search Report, Korean Intellectual Property Office, Daejeon, Republic of Korea, in PCT/2010/040578, PCT copending application, Hyun Shik Oh, Authorized Officer, Feb. 11, 2011.

International Search Report for International Application No. PCT/US2008/065022; P. Delaporte, Authorized Officer, Apr. 23, 2010.

International Search Report for International Application No. PCT/US2009/068916; Hyun Shik Oh Authorized Officer; Aug. 5, 2010.

Leznoff et al,, "Photocyclization of Aryl Polyenes. V. Photochemical Synthesis of Substituted Chrysenes," Canadian Journal of Chemistry, 1972, vol. 50, pp. 528-533.

Extended European Search Report for Application No. EP 09828227.0, counterpart to U.S. Appl. No. 13/120,001; Jul. 20, 2012.

Tokito et al., "Highly Efficient Blue-Green Emission from Organic Light-Emitting Diodes Using Dibenzochrysene Derivatives," Applied Physics Letters, 2000, vol. 77, No. 2, pp. 160-162.

Extended European Search Report for Application No. 09848342.3, counterpart to U.S. Appl. No. 12/643,487; Jan. 23, 2013.

Extended European Search Report for Application No. EP 09844464.9, counterpart to U.S. Appl. No. 12/643,511; Oct. 26, 2012.

Extended European Search Report for Application No. EP 1079464.9, counterpart to U.S. Appl. No. 13/379,807; May 3, 2013.

\* cited by examiner

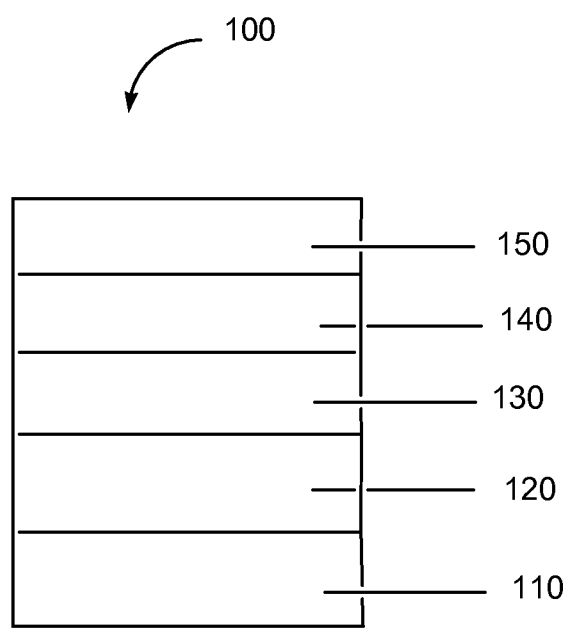

DEUTERATED COMPOUNDS FOR LUMINESCENT APPLICATIONS

RELATED APPLICATION DATA

This application claims priority under 35 U.S.C. §119(e) from U.S. Provisional Application No. 61/139,834 filed on Dec. 22, 2008, U.S. Provisional Application No. 61/176,141 filed on May 7, 2009, each of which is incorporated by reference herein in its entirety.

BACKGROUND

1. Field of the Disclosure

This invention relates to electroactive compounds which are at least partially deuterated. It also relates to electronic devices in which at least one active layer includes such a compound.

2. Description of the Related Art

Organic electronic devices that emit light, such as light-emitting diodes that make up displays, are present in many different kinds of electronic equipment. In all such devices, an organic active layer is sandwiched between two electrical contact layers. At least one of the electrical contact layers is light-transmitting so that light can pass through the electrical contact layer. The organic active layer emits light through the light-transmitting electrical contact layer upon application of electricity across the electrical contact layers.

It is well known to use organic electroluminescent compounds as the active component in light-emitting diodes. Simple organic molecules such as anthracene, thiadiazole derivatives, and coumarin derivatives are known to show electroluminescence. Semiconductive conjugated polymers have also been used as electroluminescent components, as has been disclosed in, for example, U.S. Pat. Nos. 5,247,190, 5,408,109, and Published European Patent Application 443 861.

However, there is a continuing need for electroluminescent compounds.

SUMMARY

There is provided a compound selected from the group consisting of a bis(diarylamino)anthracene and a bis(diarylamino)chrysene, wherein the compound has at least one D.

There is also provided an electronic device comprising an active layer comprising the above compound.

There is also provided a compound having Formula I or Formula II:

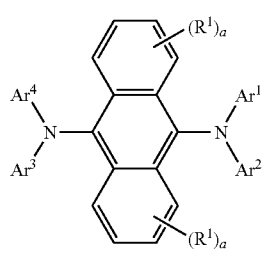

Formula I

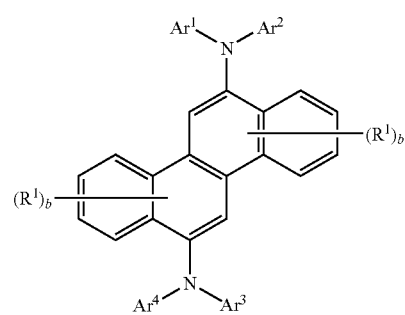

Formula II wherein:
$R^1$ is the same or different at each occurrence and is selected from the group consisting of D, alkyl, alkoxy and aryl, where adjacent $R^1$ groups may be joined together to form a 5- or 6-membered aliphatic ring;
$Ar^1$ through $Ar^4$ are the same or different and are selected from the group consisting of aryl groups;
a is the same or different at each occurrence and is an integer from 0 to 4; and
b is the same or different at each occurrence and is an integer from 0 to 5;
wherein there is at least one D.

There is also provided an electronic device comprising an active layer comprising a compound of Formula I or Formula II.

BRIEF DESCRIPTION OF THE DRAWINGS

Embodiments are illustrated in the accompanying figures to improve understanding of concepts as presented herein.

FIG. 1 includes an illustration of one example of an organic electronic device.

Skilled artisans appreciate that objects in the figures are illustrated for simplicity and clarity and have not necessarily been drawn to scale. For example, the dimensions of some of the objects in the figures may be exaggerated relative to other objects to help to improve understanding of embodiments.

DETAILED DESCRIPTION

Many aspects and embodiments are disclosed herein and are exemplary and not limiting. After reading this specification, skilled artisans appreciate that other aspects and embodiments are possible without departing from the scope of the invention.

Other features and benefits of any one or more of the embodiments will be apparent from the following detailed description, and from the claims. The detailed description first addresses Definitions and Clarification of Terms followed by the Electroactive Compound, the Electronic Device, and finally Examples.

1. Definitions and Clarification of Terms

Before addressing details of embodiments described below, some terms are defined or clarified.

As used herein, the term "aliphatic ring" is intended to mean a cyclic group that does not have delocalized pi electrons. In some embodiments, the aliphatic ring has no unsaturation. In some embodiments, the ring has one double or triple bond.

The term "alkoxy" refers to the group RO—, where R is an alkyl.

The term "alkyl" is intended to mean a group derived from an aliphatic hydrocarbon having one point of attachment, and includes a linear, a branched, or a cyclic group. The term is intended to include heteroalkyls and deuterated alkyls. The term is intended to include substituted and unsubstituted groups. The term "hydrocarbon alkyl" refers to an alkyl group having no heteroatoms. The term "deuterated alkyl" is a hydrocarbon alkyl having at least one available H replaced by D. In some embodiments, an alkyl group has from 1-20 carbon atoms.

The term "aryl" is intended to mean a group derived from an aromatic hydrocarbon having one point of attachment. The term "aromatic compound" is intended to mean an organic compound comprising at least one unsaturated cyclic group having delocalized pi electrons. The term is intended to include heteroaryls and deuterated aryls. The term "hydrocarbon aryl" is intended to mean aromatic compounds having no heteroatoms in the ring. The term aryl includes groups which have a single ring and those which have multiple rings which can be joined by a single bond or fused together. The term "deuterated aryl" refers to an aryl group having at least one of the available H atoms which is bonded directly to the aryl replaced by D. The term "arylene" is intended to mean a group derived from an aromatic hydrocarbon having two points of attachment. Any suitable ring position of the aryl moiety may be covalently linked to the defined chemical structure. In some embodiments, a hydrocarbon aryl group has from 3-60 carbon atoms; in some embodiments, 6 to 30 carbon atoms. Heteroaryl groups may have from 3-50 carbon atoms; in some embodiments, 3-30 carbon atoms.

The term "branched alkyl" refers to an alkyl group having at least one secondary or tertiary carbon. The term "secondary alkyl" refers to a branched alkyl group having a secondary carbon atom. The term "tertiary alkyl" refers to a branched alkyl group having a tertiary carbon atom. In some embodiments, the branched alkyl group is attached via a secondary or tertiary carbon.

The term "charge transport," when referring to a layer, material, member, or structure is intended to mean such layer, material, member, or structure facilitates migration of such charge through the thickness of such layer, material, member, or structure with relative efficiency and small loss of charge. Hole transport materials facilitate positive charge; electron transport material facilitate negative charge. Although light-emitting materials may also have some charge transport properties, the terms "charge, hole, or electron transport layer, material, member, or structure" are not intended to include a layer, material, member, or structure whose primary function is light emission.

The term "compound" is intended to mean an electrically uncharged substance made up of molecules that further consist of atoms, wherein the atoms cannot be separated by physical means. The phrase "adjacent to," when used to refer to layers in a device, does not necessarily mean that one layer is immediately next to another layer. On the other hand, the phrase "adjacent R groups," is used to refer to R groups that are next to each other in a chemical formula (i.e., R groups that are on atoms joined by a bond).

The term "deuterated" is intended to mean that at least one available H has been replaced by D. A compound or group that is X % deuterated, has X % of the available H replaced by D. A compound or group which is deuterated is one in which deuterium is present in at least 100 times the natural abundance level.

The term "electroactive" as it refers to a layer or a material, is intended to indicate a layer or material which electronically facilitates the operation of the device. Examples of active materials include, but are not limited to, materials which conduct, inject, transport, or block a charge, where the charge can be either an electron or a hole, or materials which emit radiation or exhibit a change in concentration of electron-hole pairs when receiving radiation. Examples of inactive materials include, but are not limited to, planarization materials, insulating materials, and environmental barrier materials.

The prefix "hetero" indicates that one or more carbon atoms have been replaced with a different atom. In some embodiments, the different atom is N, O, or S.

The term "layer" is used interchangeably with the term "film" and refers to a coating covering a desired area. The term is not limited by size. The area can be as large as an entire device or as small as a specific functional area such as the actual visual display, or as small as a single sub-pixel. Layers and films can be formed by any conventional deposition technique, including vapor deposition, liquid deposition (continuous and discontinuous techniques), and thermal transfer. Continuous deposition techniques, include but are not limited to, spin coating, gravure coating, curtain coating, dip coating, slot-die coating, spray coating, and continuous nozzle coating. Discontinuous deposition techniques include, but are not limited to, ink jet printing, gravure printing, and screen printing.

The term "organic electronic device" or sometimes just "electronic device" is intended to mean a device including one or more organic semiconductor layers or materials.

The term "oxyalkyl" is intended to mean a heteroalkyl group having one or more carbons replaced with oxygens. The term includes groups which are linked via an oxygen.

The term "silyl" refers to the group $R_3Si-$, where R is H, D, C1-20 alkyl, fluoroalkyl, or aryl. In some embodiments, one or more carbons in an R alkyl group are replaced with Si. In some embodiments, the silyl groups are $(hexyl)_2Si(Me)CH_2CH_2Si(Me)_2-$ and $[CF_3(CF_2)_6CH_2CH_2]_2SiMe-$.

The term "siloxane" refers to the group $(RO)_3Si-$, where R is H, D, C1-20 alkyl, or fluoroalkyl.

All groups can be substituted or unsubstituted unless otherwise indicated. In some embodiments, the substituents are selected from the group consisting of D, halide, alkyl, alkoxy, aryl, and cyano. An optionally substituted group, such as, but not limited to, alkyl or aryl, may be substituted with one or more substituents which may be the same or different. Other suitable substituents include nitro, cyano, $-N(R')(R'')$, hydroxy, carboxy, alkenyl, alkynyl, aryloxy, alkoxycarbonyl, perfluoroalkyl, perfluoroalkoxy, arylalkyl, silyl, siloxane, thioalkoxy, $-S(O)_2-N(R')(R'')$, $-C(=O)-N(R')(R'')$, $(R')(R'')$N-alkyl, $(R')(R'')$N-alkoxyalkyl, $(R')(R'')$ N-alkylaryloxyalkyl, $-S(O)_s$-aryl (where s=0-2) or $-S(O)_s$-heteroaryl (where s=0-2). Each R' and R" is independently an optionally substituted alkyl, cycloalkyl, or aryl group. R' and R", together with the nitrogen atom to which they are bound, can form a ring system in certain embodiments. Substituents may also be crosslinking groups. As used herein, the terms "comprises," "comprising," "includes," "including," "has,"

"having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

Also, use of "a" or "an" are employed to describe elements and components described herein. This is done merely for convenience and to give a general sense of the scope of the invention. This description should be read to include one or at least one and the singular also includes the plural unless it is obvious that it is meant otherwise.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The IUPAC numbering system is used throughout, where the groups from the Periodic Table are numbered from left to right as 1-18 (CRC Handbook of Chemistry and Physics, 81st Edition, 2000).

2. Electroactive Compound

The compound described herein is a bis(diarylamino)anthracene or a bis(diarylamino)chrysene having at least one D. In some embodiments, the compound is at least 10% deuterated; in some embodiments, at least 20% deuterated; in some embodiments, at least 30% deuterated; in some embodiments, at least 40% deuterated; in some embodiments, at least 50% deuterated; in some embodiments, at least 60% deuterated; in some embodiments, at least 70% deuterated; in some embodiments, at least 80% deuterated; in some embodiments, at least 90% deuterated.

In some embodiments, the electroactive compound has Formula I or Formula II:

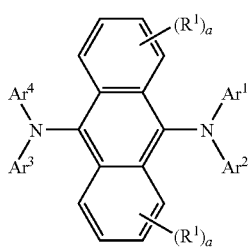

Formula I

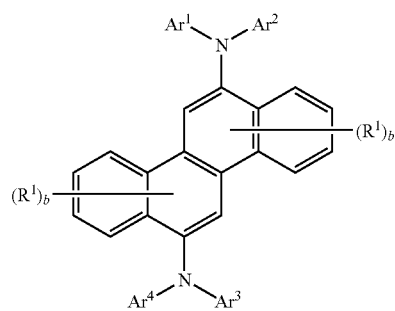

Formula II wherein:
$R^1$ is the same or different at each occurrence and is selected from the group consisting of D, alkyl, alkoxy and aryl, where adjacent $R^1$ groups may be joined together to form a 5- or 6-membered aliphatic ring;
$Ar^1$ through $Ar^4$ are the same or different and are selected from the group consisting of aryl groups;
a is the same or different at each occurrence and is an integer from 0 to 4; and
b is the same or different at each occurrence and is an integer from 0 to 5;
wherein the compound has at least one D.

In some embodiments, the compounds are capable of red, green or blue emission.

In some embodiments of Formulae I and II, the deuteration is on a substituent group on an aryl ring. The aryl group having a deuterated substituent group can be can be the core anthracene group of Formula I or the core chrysene group of Formula II; or an aryl on the nitrogen; or a substituent aryl group. In some embodiments, the deuterated substituent group on an aryl ring is selected from alkyl, aryl, alkoxy, and aryloxy. In some embodiments, the substituent groups are at least 10% deuterated; in some embodiments, at least 20% deuterated; in some embodiments, at least 30% deuterated; in some embodiments, at least 40% deuterated; in some embodiments, at least 50% deuterated; in some embodiments, at least 60% deuterated; in some embodiments, at least 70% deuterated; in some embodiments, at least 80% deuterated; in some embodiments, at least 90% deuterated.

In some embodiments of Formulae I and II, the deuteration is on any one or more of the aryl groups $Ar^1$ through $Ar^4$. In this case, at least one of $Ar^1$ through $Ar^4$ is a deuterated aryl group. In some embodiments, $Ar^1$ through $Ar^4$ are at least 10% deuterated. By this it is meant that at least 10% of all the available H bonded to aryl C in $Ar^1$ through $Ar^4$ are replaced with D. In some embodiments, each aryl ring will have some D. In some embodiments, some, and not all of the aryl rings have D. In some embodiments, $Ar^1$ through $Ar^4$ are at least 20% deuterated; in some embodiments, at least 30% deuterated; in some embodiments, at least 40% deuterated; in some embodiments, at least 50% deuterated; in some embodiments, at least 60% deuterated; in some embodiments, at least 70% deuterated; in some embodiments, at least 80% deuterated; in some embodiments, at least 90% deuterated.

In some embodiments of Formulae I and II, the deuteration is present on both the substituent groups and the aryl groups. In some embodiments, the compound of Formulae I and II is at least 10% deuterated; in some embodiments, at least 20% deuterated; in some embodiments, at least 30% deuterated; in some embodiments, at least 40% deuterated; in some embodiments, at least 50% deuterated; in some embodiments, at least 60% deuterated; in some embodiments, at least 70% deuterated; in some embodiments, at least 80% deuterated; in some embodiments, at least 90% deuterated.

In some embodiments of Formula I, both a=0.

In some embodiments of Formula I, at least one a is greater than 0. In some embodiments, at least one $R^1$ is a hydrocarbon alkyl. In some embodiments, $R^1$ is a deuterated alkyl. In some embodiments, $R^1$ is selected from a branched hydrocarbon alkyl and a cyclic hydrocarbon alkyl.

In some embodiments of Formula I, both a=4 and $R^1$ is D.

In Formula II, the bond to $(R^1)_a$ is intended to indicate that the $R^1$ group can be at any site on the two fused rings.

In some embodiments of Formula II, both b=0.

In some embodiments of Formula II, at least one b is greater than 0. In some embodiments, at least one $R^1$ is a hydrocarbon alkyl. In some embodiments, $R^1$ is selected from a branched hydrocarbon alkyl and a cyclic hydrocarbon alkyl.

In some embodiments of Formula II, both b=5 and $R^1$ is D.

In some embodiments, at least one of $Ar^1$ through $Ar^4$ has Formula III:

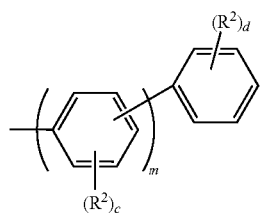

Formula III where:
  $R^2$ is the same or different at each occurrence and is selected from the group consisting of D, alkyl, alkoxy, aryl, silyl, and siloxane, or adjacent $R^2$ groups can be joined to form an aromatic ring;
  c is the same or different at each occurrence and is an integer from 0-4;
  d is the same or different at each occurrence and is an integer from 0-5; and
  m is the same or different at each occurrence and is an integer from 0 to 6.

In some embodiments, at least one of $Ar^1$ through $Ar^4$ has Formula IV:

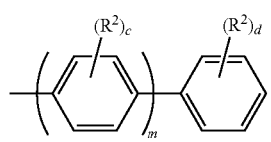

Formula IV where:
  $R^2$ is the same or different at each occurrence and is selected from the group consisting of D, alkyl, alkoxy, and aryl, or adjacent $R^2$ groups can be joined to form an aromatic ring;
  c is the same or different at each occurrence and is an integer from 0-4;
  d is the same or different at each occurrence and is an integer from 0-5; and
  m is the same or different at each occurrence and is an integer from 0 to 6.

In some embodiments, $Ar^1$ through $Ar^4$ is selected from the group consisting of phenyl, biphenyl, terphenyl, naphthyl, phenylnapthyl, naphthylphenyl, and binaphthyl.

In some embodiments, $Ar^1$ through $Ar^4$ are perdeuterated.

In some embodiments, $Ar^1$ through $Ar^4$ are perdeuterated, except for one alkyl group on a terminal aryl.

In some embodiments, the compounds are symmetrical with respect to the diarylamino groups. In this case, $Ar^1=Ar^3$, and $Ar^2=Ar^4$.

In some embodiments, the compounds are non-symmetrical with respect to the diarylamino groups. In this case, $Ar^1$ is different from both $Ar^3$ and $Ar^4$. In some embodiments, $Ar^2$ is also different from both $Ar^3$ and $Ar^4$.

Some non-limiting examples of compounds having Formula I include Compounds E1 and E2 below:

Compound E1:

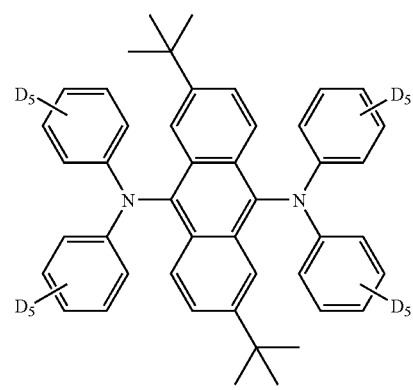

Compound E2:

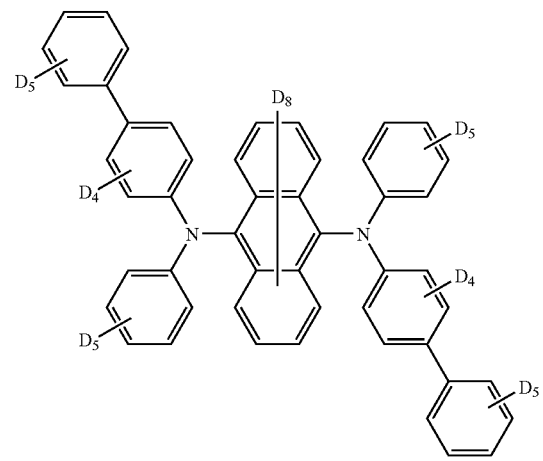

Some non-limiting examples of compounds having Formula II include Compounds E3 through E9 below:

Compound E3:
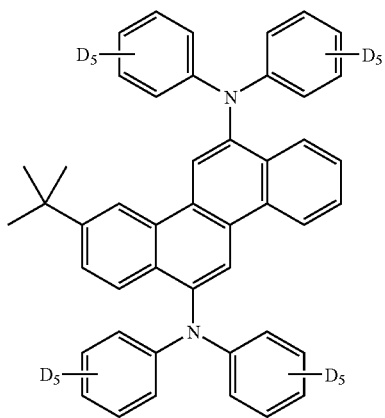
Compound E4:
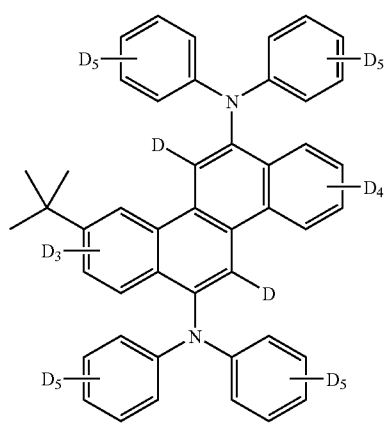
Compound E5:
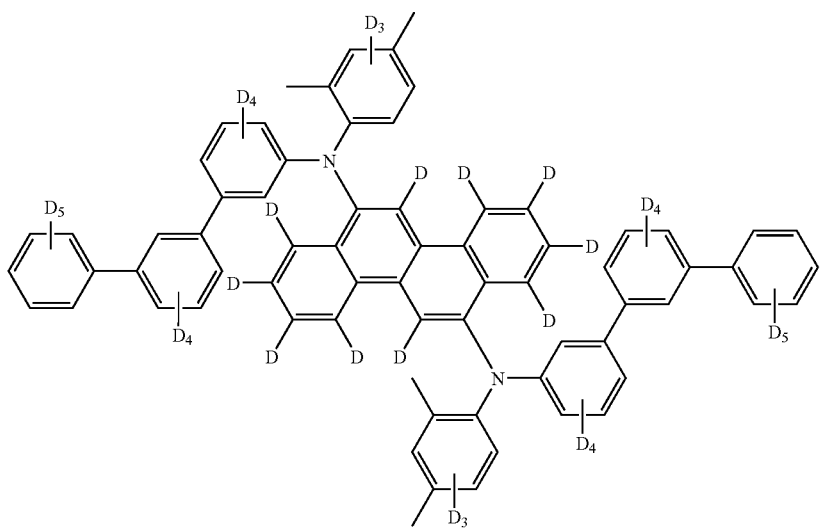
Compound E6:
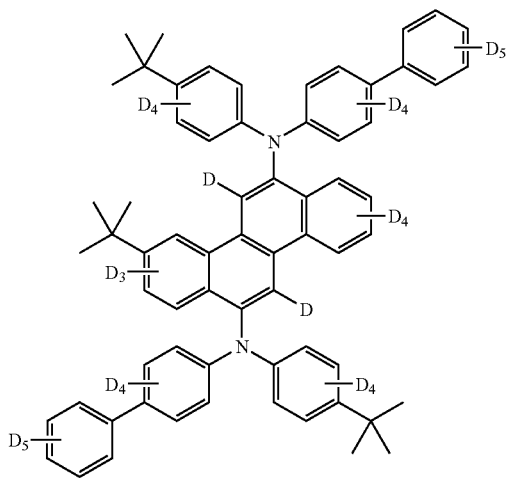
Compound E7:
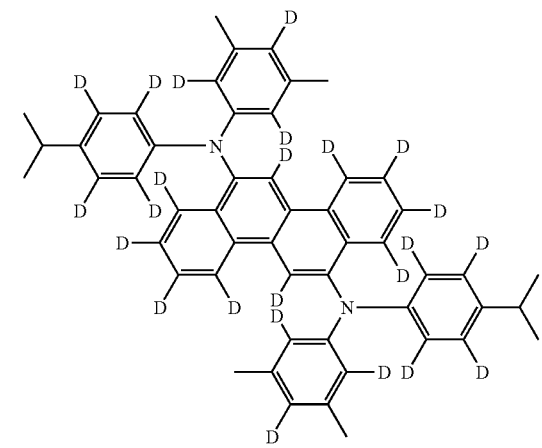

Compound E8:

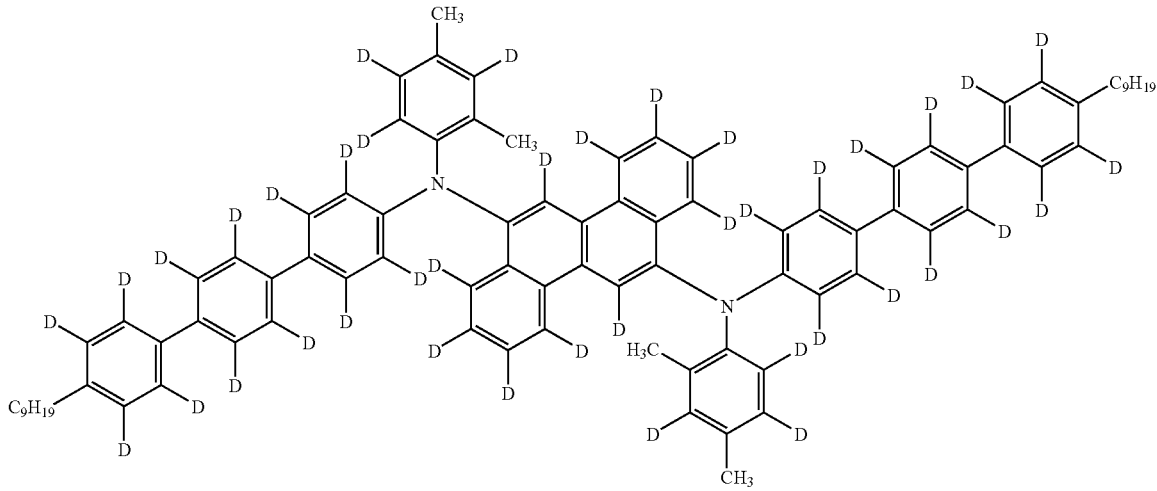

E9:

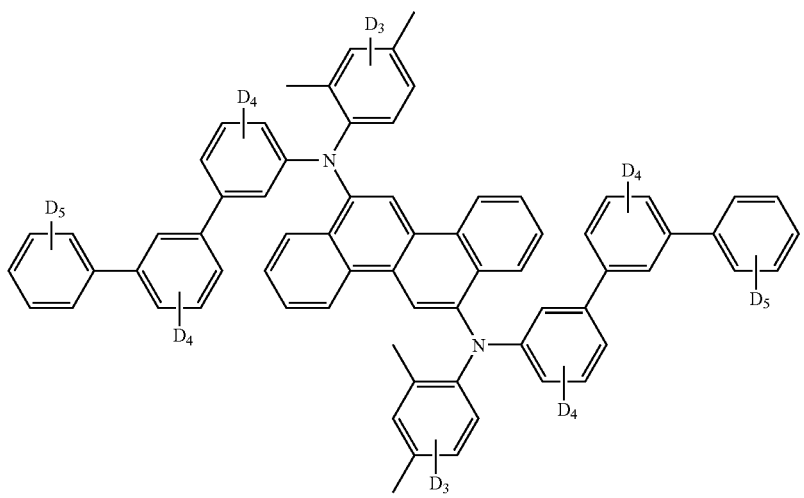

The non-deuterated analog compounds can be made using any technique that will yield a C—C or C—N bond. A variety of such techniques are known, such as Suzuki, Yamamoto, Stille, and Pd- or Ni-catalyzed C—N couplings. The new deuterated compound can then be prepared in a similar manner using deuterated precursor materials or, more generally, by treating the non-deuterated compound with deuterated solvent, such as d6-benzene, in the presence of a Lewis acid H/D exchange catalyst, such as aluminum trichloride or ethyl aluminum chloride. Exemplary preparations are given in the Examples. The level of deuteration can be determined by NMR analysis and by mass spectrometry, such as Atmospheric Solids Analysis Probe Mass Spectrometry (ASAP-MS).

The compounds described herein can be formed into films using liquid deposition techniques. Surprisingly and unexpectedly, these compounds have greatly improved properties when compared to analogous non-deuterated compounds. Electronic devices including an active layer with the compounds described herein, have greatly improved lifetimes. In addition, the lifetime increases are achieved in combination with high quantum efficiency and good color saturation. Furthermore, the deuterated compounds described herein have greater air tolerance than the non-deuterated analogs. This can result in greater processing tolerance both for the preparation and purification of the materials and in the formation of electronic devices using the materials.

The new deuterated compounds described herein have utility as hole transport materials, as electroluminescent materials, and as hosts for elecgtroluminescent materials.

3. Electronic Device

Organic electronic devices that may benefit from having one or more layers comprising the electroluminescent materials described herein include, but are not limited to, (1) devices that convert electrical energy into radiation (e.g., a light-emitting diode, light emitting diode display, or diode laser), (2) devices that detect signals through electronics processes (e.g., photodetectors, photoconductive cells, photoresistors, photoswitches, phototransistors, phototubes, IR detectors), (3) devices that convert radiation into electrical energy, (e.g., a photovoltaic device or solar cell), and (4) devices that include one or more electronic components that include one or more organic semi-conductor layers (e.g., a transistor or diode).

One illustration of an organic electronic device structure is shown in FIG. 1. The device 100 has a first electrical contact layer, an anode layer 110 and a second electrical contact layer, a cathode layer 160, and an electroactive layer 140 between them. Adjacent to the anode is a buffer layer 120. Adjacent to the buffer layer is a hole transport layer 130, comprising hole transport material. Adjacent to the cathode may be an electron transport layer 150, comprising an electron transport material. As an option, devices may use one or more additional hole injection or hole transport layers (not shown) next to the anode 110 and/or one or more additional electron injection or electron transport layers (not shown) next to the cathode 160.

Layers 120 through 150 are individually and collectively referred to as the active layers.

In one embodiment, the different layers have the following range of thicknesses: anode 110, 500-5000 Å, in one embodiment 1000-2000 Å; buffer layer 120, 50-2000 Å, in one embodiment 200-1000 Å; hole transport layer 130, 50-2000 Å, in one embodiment 200-1000 Å; electroactive layer 140, 10-2000 Å, in one embodiment 100-1000 Å; layer 150, 50-2000 Å, in one embodiment 100-1000 Å; cathode 160, 200-10000 Å, in one embodiment 300-5000 Å. The location of the electron-hole recombination zone in the device, and thus the emission spectrum of the device, can be affected by the relative thickness of each layer. The desired ratio of layer thicknesses will depend on the exact nature of the materials used.

Depending upon the application of the device 100, the electroactive layer 140 can be a light-emitting layer that is activated by an applied voltage (such as in a light-emitting diode or light-emitting electrochemical cell), or a layer of material that responds to radiant energy and generates a signal with or without an applied bias voltage (such as in a photodetector). Examples of photodetectors include photoconductive cells, photoresistors, photoswitches, phototransistors, and phototubes, and photovoltaic cells, as these terms are described in Markus, John, *Electronics and Nucleonics Dictionary*, 470 and 476 (McGraw-Hill, Inc. 1966).

In some embodiments, the new deuterated compounds are useful as hole transport materials in layer 130. In some embodiments, at least one additional layer includes a deuterated material. In some embodiments, the additional layer is the buffer layer 120. In some embodiments, the additional layer is the electroactive layer 140. In some embodiments, the additional layer is the electron transport layer 150.

In some embodiments, the new deuterated compounds are useful as host materials for electroactive materials in electroactive layer 140. In some embodiments, the emissive material is also deuterated. In some embodiments, at least one additional layer includes a deuterated material. In some embodiments, the additional layer is the buffer layer 120. In some embodiments, the additional layer is the hole transport layer 130. In some embodiments, the additional layer is the electron transport layer 150.

In some embodiments, the new deuterated compounds are useful as electroactive materials in electroactive layer 140. In some embodiments, a host is also present in the electroactive layer. In some embodiments, the host material is also deuterated. In some embodiments, at least one additional layer includes a deuterated material. In some embodiments, the additional layer is the buffer layer 120. In some embodiments, the additional layer is the hole transport layer 130. In some embodiments, the additional layer is the electron transport layer 150

In some embodiments, the new deuterated compounds are useful as electron transport materials in layer 150. In some embodiments, at least one additional layer includes a deuterated material. In some embodiments, the additional layer is the buffer layer 120. In some embodiments, the additional layer is the hole transport layer 130. In some embodiments, the additional layer is the electroactive layer 140.

In some embodiments, an electronic device has deuterated materials in any combination of layers selected from the group consisting of the buffer layer, the hole transport layer, the electroactive layer, and the electron transport layer.

In some embodiments, the devices have additional layers to aid in processing or to improve functionality. Any or all of these layers can include deuterated materials. In some embodiments, all the organic device layers comprise deuterated materials. In some embodiments, all the organic device layers consist essentially of deuterated materials.

a. Electroactive Layer

The new deuterated compounds described herein are useful as electroactive materials in layer 140. The compounds can be used alone, or in combination with a host material.

In some embodiments, the electroactive layer consists essentially of a host material and the new deuterated compound described herein.

In some embodiments, the host is a bis-condensed cyclic aromatic compound.

In some embodiments, the host is an anthracene derivative compound. In some embodiments the compound has the formula:

where:
An is an anthracene moiety;
L is a divalent connecting group.

In some embodiments of this formula, L is a single bond, —O—, —S—, —N(R)—, or an aromatic group. In some embodiments, An is a mono- or diphenylanthryl moiety.

In some embodiments, the host has the formula:

where:
An is an anthracene moiety;
A is the same or different at each occurrence and is an aromatic group.

In some embodiments, the A groups are attached at the 9- and 10-positions of the anthracene moiety. In some embodiments, A is selected from the group consisting naphthyl, naphthylphenylene, and naphthylnaphthylene. In some embodiments the compound is symmetrical and in some embodiments the compound is non-symmetrical.

In some embodiments, the host has the formula:

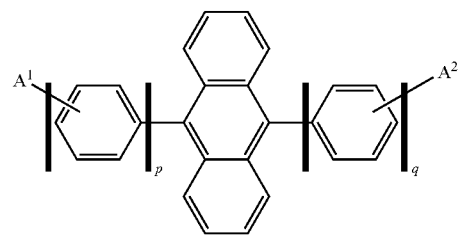

where:
$A^1$ and $A^2$ are the same or different at each occurrence and are selected from the group consisting of H, an aromatic group, an alkyl group and an alkenyl group, or A may represent one or more fused aromatic rings;
p and q are the same or different and are an integer from 1-3.

In some embodiments, the anthracene derivative is non-symmetrical. In some embodiments, p=2 and q=1.

In some embodiments, at least one of A¹ and A² is a naphthyl group. In some embodiments, additional substituents are present.

In some embodiments, the host is selected from the group consisting of

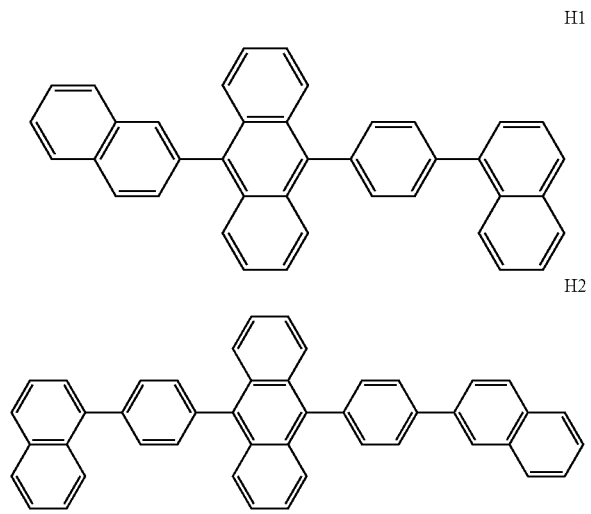

and combinations thereof.

The new deuterated compounds described herein, in addition to being useful as electroactive materials in the electroactive layer, can also act as charge carrying hosts for other electroactive materials in the electroactive layer 140. In some embodiments, the electroactive layer consists essentially of the new deuterated material and one or more electroactive materials.

b. Other Device Layers

The other layers in the device can be made of any materials that are known to be useful in such layers.

The anode 110, is an electrode that is particularly efficient for injecting positive charge carriers. It can be made of, for example, materials containing a metal, mixed metal, alloy, metal oxide or mixed-metal oxide, or it can be a conducting polymer, or mixtures thereof. Suitable metals include the Group 11 metals, the metals in Groups 4-6, and the Group 8-10 transition metals. If the anode is to be light-transmitting, mixed-metal oxides of Groups 12, 13 and 14 metals, such as indium-tin-oxide, are generally used. The anode 110 can also comprise an organic material such as polyaniline as described in "Flexible light-emitting diodes made from soluble conducting polymer," *Nature* vol. 357, pp 477-479 (11 Jun. 1992). At least one of the anode and cathode is desirably at least partially transparent to allow the generated light to be observed.

The buffer layer 120 comprises buffer material and may have one or more functions in an organic electronic device, including but not limited to, planarization of the underlying layer, charge transport and/or charge injection properties, scavenging of impurities such as oxygen or metal ions, and other aspects to facilitate or to improve the performance of the organic electronic device. Buffer materials may be polymers, oligomers, or small molecules. They may be vapour deposited or deposited from liquids which may be in the form of solutions, dispersions, suspensions, emulsions, colloidal mixtures, or other compositions.

The buffer layer can be formed with polymeric materials, such as polyaniline (PANI) or polyethylenedioxythiophene (PEDOT), which are often doped with protonic acids. The protonic acids can be, for example, poly(styrenesulfonic acid), poly(2-acrylamido-2-methyl-1-propanesulfonic acid), and the like.

The buffer layer can comprise charge transfer compounds, and the like, such as copper phthalocyanine and the tetrathiafulvalene-tetracyanoquinodimethane system (TTF-TCNQ).

In some embodiments, the buffer layer comprises at least one electrically conductive polymer and at least one fluorinated acid polymer. Such materials have been described in, for example, published U.S. patent applications 2004-0102577, 2004-0127637, and 2005/205860

In some embodiments, the new deuterated compounds described herein have utility as hole transport materials. Examples of other hole transport materials for layer 130 have been summarized for example, in Kirk-Othmer Encyclopedia of Chemical Technology, Fourth Edition, Vol. 18, p. 837-860, 1996, by Y. Wang. Both hole transporting molecules and polymers can be used. Commonly used hole transporting molecules are: N,N'-diphenyl-N,N'-bis(3-methylphenyl)-[1,1'-biphenyl]-4,4'-diamine (TPD), 1,1-bis[(di-4-tolylamino)phenyl]cyclohexane (TAPC), N,N'-bis(4-methylphenyl)-N,N'-bis(4-ethylphenyl)-[1,1'-(3,3'-dimethyl)biphenyl]-4,4'-diamine (ETPD), tetrakis-(3-methylphenyl)—N,N,N',N'-2,5-phenylenediamine (PDA), a-phenyl-4-N,N-diphenylaminostyrene (TPS), p-(diethylamino)benzaldehyde diphenylhydrazone (DEH), triphenylamine (TPA), bis[4-(N,N-diethylamino)-2-methylphenyl](4-methylphenyl)methane (MPMP), 1-phenyl-3-[p-(diethylamino)styryl]-5-[p-(diethylamino)phenyl]pyrazoline (PPR or DEASP), 1,2-trans-bis(9H-carbazol-9-yl)cyclobutane (DCZB), N,N,N',N'-tetrakis(4-methylphenyl)-(1,1'-biphenyl)-4,4'-diamine (TTB), N,N'-bis(naphthalen-1-yl)—N,N'-bis-(phenyl)benzidine (α-NPB), and porphyrinic compounds, such as copper phthalocyanine. Commonly used hole transporting polymers are polyvinylcarbazole, (phenylmethyl)-polysilane, and polyaniline. It is also possible to obtain hole transporting polymers by doping hole transporting molecules such as those mentioned above into polymers such as polystyrene and polycarbonate. In some cases, triarylamine polymers are used, especially triarylamine-fluorene copolymers. In some cases, the polymers and copolymers are crosslinkable. Examples of crosslinkable hole transport polymers can be found in, for example, published US patent application 2005-0184287 and published PCT application WO 2005/052027. In some embodiments, the hole transport layer is doped with a p-dopant, such as tetrafluorotetracyanoquinodimethane and perylene-3,4,9,10-tetracarboxylic-3,4,9,10-dianhydride.

In some embodiments, the new deuterated compounds described herein have utility as electron transport materials. Examples of other electron transport materials which can be used in layer 150 include metal chelated oxinoid compounds, such as tris(8-hydroxyquinolato)aluminum (Alq₃); bis(2-methyl-8-quinolinolato)(para-phenyl-phenolato)aluminum(III) (BAlQ); and azole compounds such as 2-(4-biphenyl)-5-(4-t-butylphenyl)-1,3,4-oxadiazole (PBD) and 3-(4-biphenylyl)-4-phenyl-5-(4-t-butylphenyl)-1,2,4-triazole (TAZ), and 1,3,5-tri(phenyl-2-benzimidazole)benzene (TPBI); quinoxaline derivatives such as 2,3-bis(4-fluorophenyl)quinoxaline; phenanthroline derivatives such as 9,10-diphenylphenanthroline (DPA) and 2,9-dimethyl-4,7-diphenyl-1,10-phenanthroline (DDPA); and mixtures thereof. The electron-transport layer may also be doped with n-dopants, such as Cs or other alkali metals. Layer 150 can function both to facilitate electron transport, and also serve as a buffer layer or confinement layer to prevent quenching of the exciton at layer interfaces. Preferably, this layer promotes electron mobility and reduces exciton quenching.

The cathode 160, is an electrode that is particularly efficient for injecting electrons or negative charge carriers. The cathode can be any metal or nonmetal having a lower work function than the anode. Materials for the cathode can be selected from alkali metals of Group 1 (e.g., Li, Cs), the Group 2 (alkaline earth) metals, the Group 12 metals, including the rare earth elements and lanthanides, and the actinides. Materials such as aluminum, indium, calcium, barium, samarium and magnesium, as well as combinations, can be used. Li— or Cs-containing organometallic compounds, LiF, CsF, and $Li_2O$ can also be deposited between the organic layer and the cathode layer to lower the operating voltage.

It is known to have other layers in organic electronic devices. For example, there can be a layer (not shown) between the anode 110 and buffer layer 120 to control the amount of positive charge injected and/or to provide bandgap matching of the layers, or to function as a protective layer. Layers that are known in the art can be used, such as copper phthalocyanine, silicon oxy-nitride, fluorocarbons, silanes, or an ultra-thin layer of a metal, such as Pt. Alternatively, some or all of anode layer 110, active layers 120, 130, 140, and 150, or cathode layer 160, can be surface-treated to increase charge carrier transport efficiency. The choice of materials for each of the component layers is preferably determined by balancing the positive and negative charges in the emitter layer to provide a device with high electroluminescence efficiency.

It is understood that each functional layer can be made up of more than one layer.

The device can be prepared by a variety of techniques, including sequential vapor deposition of the individual layers on a suitable substrate. Substrates such as glass, plastics, and metals can be used. Conventional vapor deposition techniques can be used, such as thermal evaporation, chemical vapor deposition, and the like. Alternatively, the organic layers can be applied from solutions or dispersions in suitable solvents, using conventional coating or printing techniques, including but not limited to spin-coating, dip-coating, roll-to-roll techniques, ink-jet printing, screen-printing, gravure printing and the like.

To achieve a high efficiency LED, the HOMO (highest occupied molecular orbital) of the hole transport material desirably aligns with the work function of the anode, and the LUMO (lowest un-occupied molecular orbital) of the electron transport material desirably aligns with the work function of the cathode. Chemical compatibility and sublimation temperature of the materials are also important considerations in selecting the electron and hole transport materials.

It is understood that the efficiency of devices made with the chrysene compounds described herein, can be further improved by optimizing the other layers in the device. For example, more efficient cathodes such as Ca, Ba or LiF can be used. Shaped substrates and novel hole transport materials that result in a reduction in operating voltage or increase quantum efficiency are also applicable. Additional layers can also be added to tailor the energy levels of the various layers and facilitate electroluminescence.

The compounds of the invention often are fluorescent and photoluminescent and can be useful in applications other than OLEDs, such as oxygen sensitive indicators and as fluorescent indicators in bioassays.

EXAMPLES

The following examples illustrate certain features and advantages of the present invention. They are intended to be illustrative of the invention, but not limiting. All percentages are by weight, unless otherwise indicated.

Comparative Example A

This example illustrates the preparation of a non-deuterated electroluminescent material, Comparative Compound A.

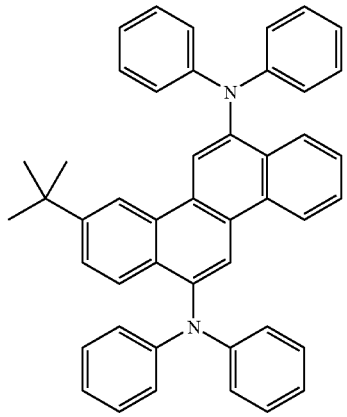 [SMILES: CC(C)(C)c1ccc2c(N(c3ccccc3)c3ccccc3)cc3c4ccccc4c(N(c4ccccc4)c4ccccc4)cc3c2c1]

(a) Preparation of 1-(4-tert-butylstyryl)naphthalene.

An oven-dried 500 ml three-neck round bottom flask was equipped with a magnetic stir bar, addition funnel and nitrogen inlet connector. The flask was charged with (1-napthylmethyl)triphenylphosphonium chloride (12.07 g, 27.5 mmol) and 200 ml of anhydrous THF. Sodium hydride (1.1 g, 25 mmol) was added in one portion. The mixture became bright orange and was left to stir overnight at room temperature. A solution of 4-tert-butyl-benzaldehyde (7.1 g, 25 mmol) in anhydrous THF (30 ml) was added to the addition funnel with a cannula. The aldehyde solution was added to the reaction mixture dropwise over 45 minutes. Reaction was left to stir at room temperature for 24 hours (orange color went away). Silica gel was added to the reaction mixture and volatiles were removed under reduced pressure. The crude product was purified by column chromatography on silica gel using 5-10% dichloromethane in hexanes. The product was isolated as a mixture of cis- and trans-isomers (6.3 g, 89%) and used without separation. The structure was confirmed by $^1H$ NMR.

(b) Preparation of 3-tert-butylchrysene.

1-(4-tert-Butylstyryl)naphthalenes (4.0 g, 14.0 mmol) were dissolved in dry toluene (1 l) in a one-liter photochemical vessel, equipped with nitrogen inlet and a stirbar. A bottle of dry propylene oxide was cooled in ice-water before 100 ml of the epoxide was withdrawn with a syringe and added to the reaction mixture. Iodine (3.61 g, 14.2 mmol) was added last. Condenser was attached on top of the photochemical vessel and halogen lamp (Hanovia, 450 W) was turned on. Reaction was stopped by turning off the lamp when no more iodine was left in the reaction mixture, as evidenced by the disappearance of its color. The reaction was complete in 3.5 hours. Toluene and excess propylene oxide were removed under reduced pressure to yield a dark yellow solid. Crude product was dissolved in a small amount of 25% dichloromethane in hexane, passed through a 4" plug of neutral alumina, and washed with 25% dichloromethane in hexane (about one liter). Volatiles were removed to give 3.6 g (91%) of 3-tert-butylchrysene as a yellow solid. The structure was confirmed by $^1H$ NMR.

(c) Preparation of 6,12-dibromo-3-tert-butylchrysene 3-tert-Butylchrysene (4.0 g, 14.1 mmol) and trimethylphosphate (110 ml) were mixed in a 500 ml round-bottom flask. After bromine (4.95 g, 31 mmol) was added, a reflux condenser was attached to the flask and reaction mixture was stirred for one hour in an oil bath at 105° C. A white precipitate formed almost immediately. Reaction mixture was worked up by pouring it onto a small amount of ice water (100 ml). The mixture was vacuum-filtered and washed well with water. The resulting tan solid was dried under vacuum. The crude product was boiled in methanol (100 ml), cooled to room temperature and filtered again to yield 3.74 g (60%) of a white solid. The structure was confirmed by $^1$H NMR.

(d) Preparation of 3-tert-butyl-$N^6,N^6, N^{12}, N^{12}$-tetraphenyl-chrysene-6,12-diamine, Comparative Compound A.

In a drybox, 6,12-dibromo-3-tert-butylchrysene (0.8 g, 1.81 mmol) and diphenylamine (1.22 g, 7.2 mmol) were combined in a 500 ml round-bottom flask and dissolved in 10 ml of dry toluene. 2-Biphenyl-di-tert-butylphosphine (0.072 g, 0.04 mmol) and tris(dibenzylideneacetone)dipalladium(0) (0.036 g, 0.02 mmol) were dissolved in 5 ml of dry toluene and stirred for 10 minutes. The catalyst solution was added to the reaction mixture, stirred for 10 minutes and followed by sodium tert-butoxide (0.35 g, 3.62 mmol) and 5 ml of dry toluene. After another 10 minutes, the reaction flask was brought out of the drybox, attached to a nitrogen line and stirred at 110° C. overnight. Next day, reaction mixture was cooled to room temperature and filtered through a two-inch plug of silica gel and Celite, washing with 500 ml of dichloromethane. Removal of volatiles under reduced pressure gave a dark brown oil. The crude product was further purified by flash chromatography on silica gel using Isolera purification system from Biotage. The resulting solid was washed with methanol and then recrystallized from hot hexane to yield 0.26 g (25%) of the product. The structure was confirmed by $^1$H NMR.

Example 1

This example illustrates the preparation of a compound having Formula II, Compound E3.

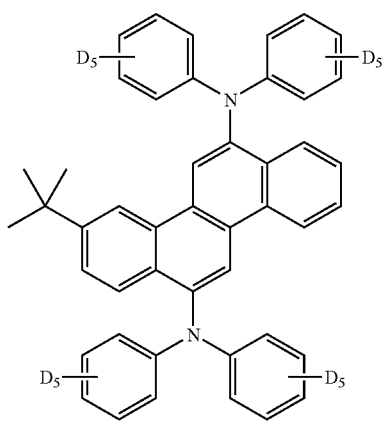

This compound was prepared from 6,12-dibromo-3-tert-butylchrysene and di(perdeuterophenyl)amine using the procedure described above for Comparative Compound A. Yield 0.37 g (36%). The structure of Compound E3 was confirmed by $^1$H NMR.

Comparative Example B

This example illustrates the preparation of a non-deuterated electroluminescent material, Comparative Compound B

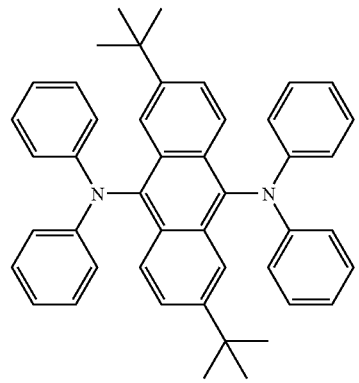 [SMILES: CC(C)(C)c1ccc2c(N(c3ccccc3)c3ccccc3)c3cc(C(C)(C)C)ccc3c(N(c3ccccc3)c3ccccc3)c2c1]

0.45 g of 2,6-di-t-butyl-9,10-dibromoanthracene (1 mM) (Müller, U.; Adam, M.; Müllen, K. Chem. Ber. 1994, 127, 437-444) was placed in a round bottom flask in a nitrogen filled glove box and 0.38 g (2.2 mM) diphenylamine and 0.2 g sodium tert-butoxide (2 mM) with 40 mL toluene were added. 0.15 g Pd$_2$ DBA$_3$ (0.15 mM) and 0.07 g P(t-Bu)3 (0.3 mM) were dissolved in 10 mL toluene and added to the first solution with stirring. When all materials are mixed the solution slowly exotherms and becomes yellow brown. The solution was stirred and heated in the glove box at 80° C. under nitrogen for 1 hr. The solution immediately is dark purple but on reaching ~80° C. it is dark yellow green with a noticeable green luminescence. After cooling to room temperature the solution is removed from the glove box and filtered through a short basic-alumina plug eluting with toluene to give a bright yellow-green band. Evaporation and recrystallization from toluene/methanol gave the expected product as confirmed by 1-H nmr, in yield of 0.55 g Example 2

This example illustrates the preparation of a compound having Formula I, Compound E1.

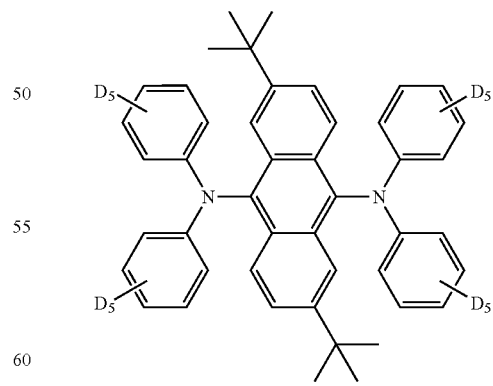

This compound was prepared from 9,10-dibromo-2,6-di-tert-butylanthracene and di(perdeuterophenyl)amine using the procedure described above for Comparative Compound B. Yield 0.55 g. The structure of Compound E1 was confirmed by $^1$H NMR.

Example 3 and Comparative Example C

These examples demonstrate the fabrication and performance of a device with a blue emitter. The following materials were used:

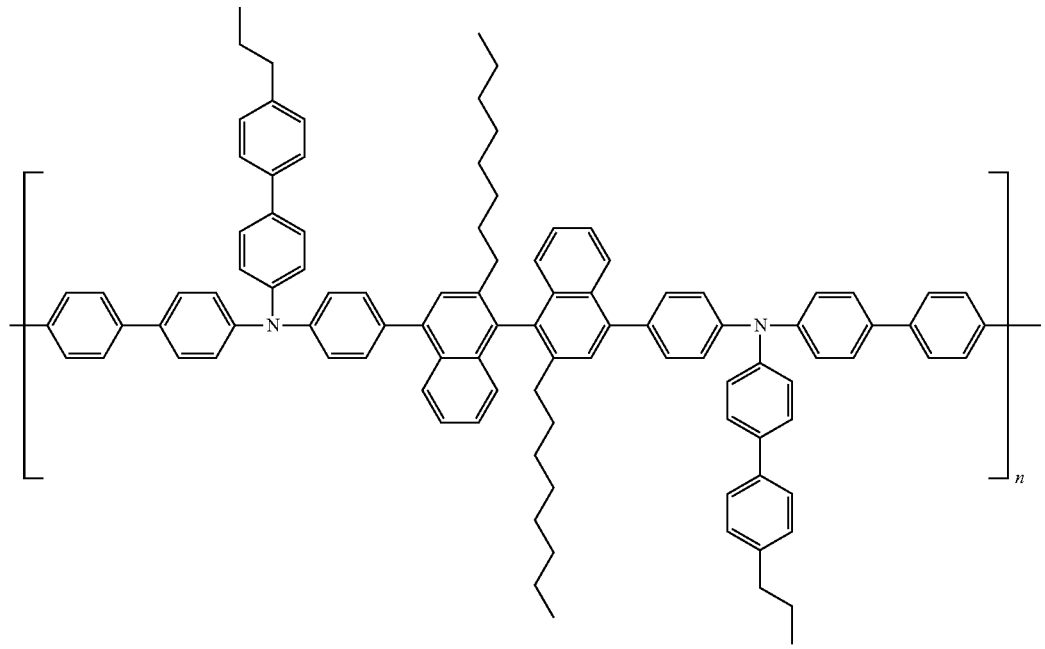

P1

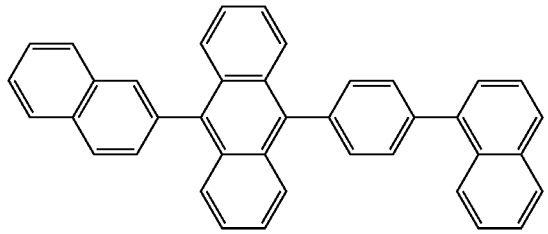

H1

The device had the following structure on a glass substrate:
anode=Indium Tin Oxide (ITO): 50 nm
buffer layer=Buffer 1 (50 nm), which is an aqueous dispersion of an electrically conductive polymer and a polymeric fluorinated sulfonic acid. Such materials have been described in, for example, published U.S. patent applications US 2004/0102577, US 2004/0127637, and US 2005/0205860.
hole transport layer=polymer P1 (20 nm)
electroactive layer=13:1 host H1:dopant (40 nm)
electron transport layer=a metal quinolate derivative (10 nm)
cathode=CsF/Al (0.7/100 nm)

OLED devices were fabricated by a combination of solution processing and thermal evaporation techniques. Patterned indium tin oxide (ITO) coated glass substrates from Thin Film Devices, Inc were used. These ITO substrates are based on Corning 1737 glass coated with ITO having a sheet resistance of 30 ohms/square and 80% light transmission. The patterned ITO substrates were cleaned ultrasonically in aqueous detergent solution and rinsed with distilled water. The patterned ITO was subsequently cleaned ultrasonically in acetone, rinsed with isopropanol, and dried in a stream of nitrogen.

Immediately before device fabrication the cleaned, patterned ITO substrates were treated with UV ozone for 10 minutes. Immediately after cooling, an aqueous dispersion of Buffer 1 was spin-coated over the ITO surface and heated to remove solvent. After cooling, the substrates were then spin-coated with a solution of a hole transport material, and then heated to remove solvent. After cooling the substrates were spin-coated with the emissive layer solution, and heated to remove solvent. The substrates were masked and placed in a vacuum chamber. The electron transport layer was deposited by thermal evaporation, followed by a layer of CsF. Masks were then changed in vacuo and a layer of Al was deposited by thermal evaporation. The chamber was vented, and the devices were encapsulated using a glass lid, dessicant, and UV curable epoxy.

The OLED samples were characterized by measuring their (1) current-voltage (I-V) curves, (2) electroluminescence radiance versus voltage, and (3) electroluminescence spectra versus voltage. All three measurements were performed at the same time and controlled by a computer. The current efficiency of the device at a certain voltage is determined by dividing the electroluminescence radiance of the LED by the current density needed to run the device. The unit is a cd/A. The power efficiency is the current efficiency divided by the operating voltage.

The unit is lm/W. The device data is given in Table 1.

TABLE 1

| | | Device Performance | | | | |
|---|---|---|---|---|---|---|
| Example | Dopant | CE [cd/A] | Voltage (V) | CIE [x] | CIE [y] | Lum. ½ Life [h] |
| Comp. Ex. C | Comparative A | 2.9 | 4.9 | 0.144 | 0.080 | 400 |
| Ex. 3 | Compound E3 | 2.9 | 4.9 | 0.145 | 0.081 | 1175 |

* All data @ 1000 nits, CE = current efficiency; CIEx and CIEy are the x and y color coordinates according to the C.I.E. chromaticity scale (Commission Internationale de L'Eclairage, 1931). Lum. ½ Life is defined as the time in hours for a device to reach one-half the initial luminance.

The relative lifetime of devices made with the chrysene dopants having Formula II are significantly better than devices made with comparative Compound A.

Example 4 and Comparative Example D

These examples demonstrate the fabrication and performance of a device with a green emitter.
The device had the following structure on a glass substrate:
anode=ITO (180 nm)
buffer layer=Buffer 1 (50 nm)
hole transport layer=polymer P1 (20 nm)
electroactive layer=13:1 host H1:dopant (60 nm)
electron transport layer=a metal quinolate derivative (10 nm)
cathode=CsF/Al (1.0/100 nm)
OLED devices were fabricated as described above for Example 3. The device data (average of three devices) is given in Table 2.

TABLE 2

| | | Device Performance | | | | |
|---|---|---|---|---|---|---|
| Example | Dopant | CE [cd/A] | Voltage (V) | CIE [x] | CIE [y] | Lum. ½ Life [h] |
| Comp. Ex. D | Comparative B | 15.5 | 4.7 | 0.20 | 0.61 | 19,494 |
| Ex. 2 | Compound E1 | 17.5 | 4.3 | 0.19 | 0.60 | 56,670 |

The relative lifetime of devices made with the anthracene dopants having Formula I are significantly better than devices made with the anthracene dopant comparative Compound B.

Note that not all of the activities described above in the general description or the examples are required, that a portion of a specific activity may not be required, and that one or more further activities may be performed in addition to those described. Still further, the order in which activities are listed are not necessarily the order in which they are performed.

In the foregoing specification, the concepts have been described with reference to specific embodiments. However, one of ordinary skill in the art appreciates that various modifications and changes can be made without departing from the scope of the invention as set forth in the claims below. Accordingly, the specification and figures are to be regarded in an illustrative rather than a restrictive sense, and all such modifications are intended to be included within the scope of invention.

Benefits, other advantages, and solutions to problems have been described above with regard to specific embodiments. However, the benefits, advantages, solutions to problems, and any feature(s) that may cause any benefit, advantage, or solution to occur or become more pronounced are not to be construed as a critical, required, or essential feature of any or all the claims.

It is to be appreciated that certain features are, for clarity, described herein in the context of separate embodiments, may also be provided in combination in a single embodiment. Conversely, various features that are, for brevity, described in the context of a single embodiment, may also be provided separately or in any subcombination. Further, reference to values stated in ranges include each and every value within that range.

What is claimed is:

1. A compound represented by Formula II:

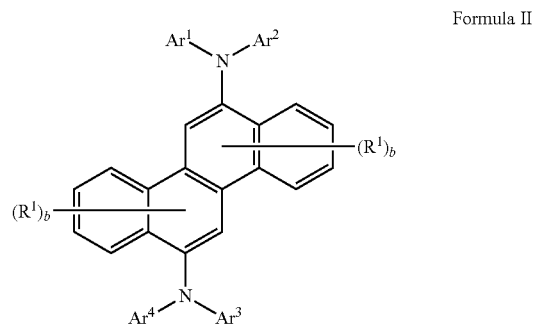

Formula II wherein:
R$^1$ is the same or different at each occurrence and is selected from the group consisting of D, alkyl, alkoxy and aryl, where adjacent R$^1$ groups may be joined together to form a 5- or 6-membered aliphatic ring;
Ar$^1$ through Ar$^4$ are the same or different and are selected from the group consisting of aryl groups; and
b is the same or different at each occurrence and is an integer from 0 to 5;
wherein at least one b is greater than 0 and at least one R$^1$ is selected from the group consisting of alkyl, alkoxy and aryl, where adjacent R$^1$ groups may be joined together to form a 5- or 6-membered aliphatic ring; and
wherein the compound is at least 10% deuterated.

2. The compound of claim 1, having at least one substituent group on an aryl ring, wherein deuteration is on the substituent group on an aryl ring.

3. The compound of claim 1, wherein at least one of Ar$^1$ through Ar$^4$ is a deuterated aryl group.

4. The compound of claim 3, wherein Ar$^1$ through Ar$^2$ are at least 20% deuterated.

5. The compound of claim 1, having at least one substituent group on an aryl ring, wherein deuteration is present on both at least one substituent group and at least one aryl ring.

6. The compound of claim 1, wherein R$^1$ is a hydrocarbon alkyl.

7. The compound of claim 1, wherein R$^1$ is a deuterated alkyl.

8. The compound of claim 1 represented by Formula II, wherein b=5 and R$^1$ is D.

9. The compound of claim 1, wherein Ar$^1$ through Ar$^4$ is selected from the group consisting of naphthyl, phenylnapthyl, naphthylphenyl, binaphthyl, and a group represented by Formula III:

Formula III

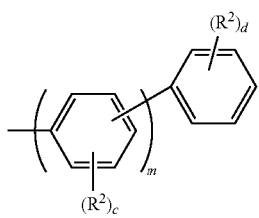

where:
R² is the same or different at each occurrence and is selected from the group consisting of D, alkyl, alkoxy, aryl, silyl, and siloxane, or adjacent R² groups can be joined to form an aromatic ring;
c is the same or different at each occurrence and is an integer from 0-4;
d is the same or different at each occurrence and is an integer from 0-5; and
m is the same or different at each occurrence and is an integer from 0 to 6.

10. The compound of claim 1, wherein $Ar^1$ through $Ar^4$ are perdeuterated.

11. A compound selected from Compounds E3, E4, and E6

Compound E3

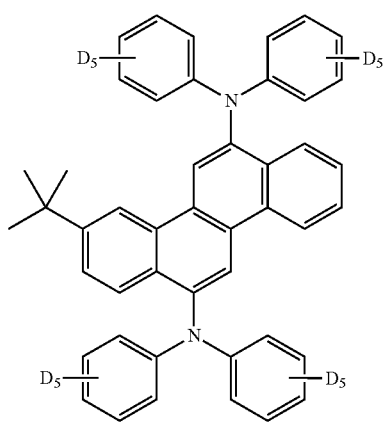

Compound E4

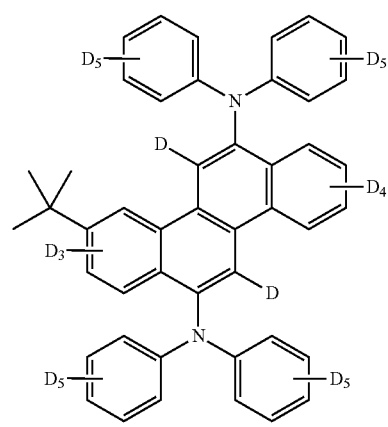

Compound E6

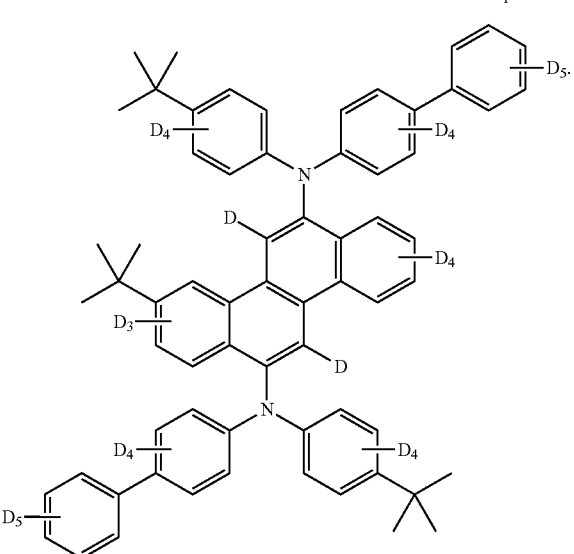

12. The compound of claim 1, having at least 50% deuteration.

13. The compound of claim 1, having at least 70% deuteration.

* * * * *